united States Patent [19]

Hirschman

[11] 3,983,873

[45] Oct. 5, 1976

[54] FEMININE HYGIENIC PAD

[76] Inventor: Shalom Z. Hirschman, 110-11 Queens Blvd., Forest Hills, N.Y. 11375

[22] Filed: July 3, 1974

[21] Appl. No.: 485,374

[52] U.S. Cl. ............................. 128/285; 128/270; 128/290 R
[51] Int. Cl.² .................... A61F 13/20; A61F 13/16
[58] Field of Search ............... 128/285, 270, 290 R, 128/290 W, 290 H

[56] References Cited
UNITED STATES PATENTS

| | | | |
|---|---|---|---|
| 882,301 | 3/1908 | Doyle | 128/290 R |
| 1,503,361 | 7/1924 | Gimurtsina | 128/290 H |
| 2,331,355 | 10/1943 | Strongson | 128/285 X |
| 2,662,527 | 12/1953 | Jacks | 128/290 R |
| 2,682,875 | 7/1954 | Brown | 128/285 |
| 2,771,882 | 11/1956 | Leupold | 128/290 R |
| 2,917,049 | 12/1959 | Delaney | 128/285 |
| 2,964,039 | 12/1960 | Johnson, Jr. et al. | 128/290 R |
| 3,183,909 | 5/1965 | Roehr | 128/290 R |
| 3,406,689 | 10/1968 | Hicks et al. | 128/290 R |
| 3,420,235 | 1/1969 | Harmon | 128/290 R |
| 3,528,422 | 9/1970 | Hodas | 128/290 R |

Primary Examiner—Aldrich F. Medbery

[57] ABSTRACT

A feminine hygienic pad for insertion into the interlabial space; the pad having a geometric configuration which (1) facilitates insertion of the pad into the interlabial space; and (2) has an improved retention within the space notwithstanding a substantial increase in weight of the pad upon absorption of discharged liquid.

23 Claims, 20 Drawing Figures

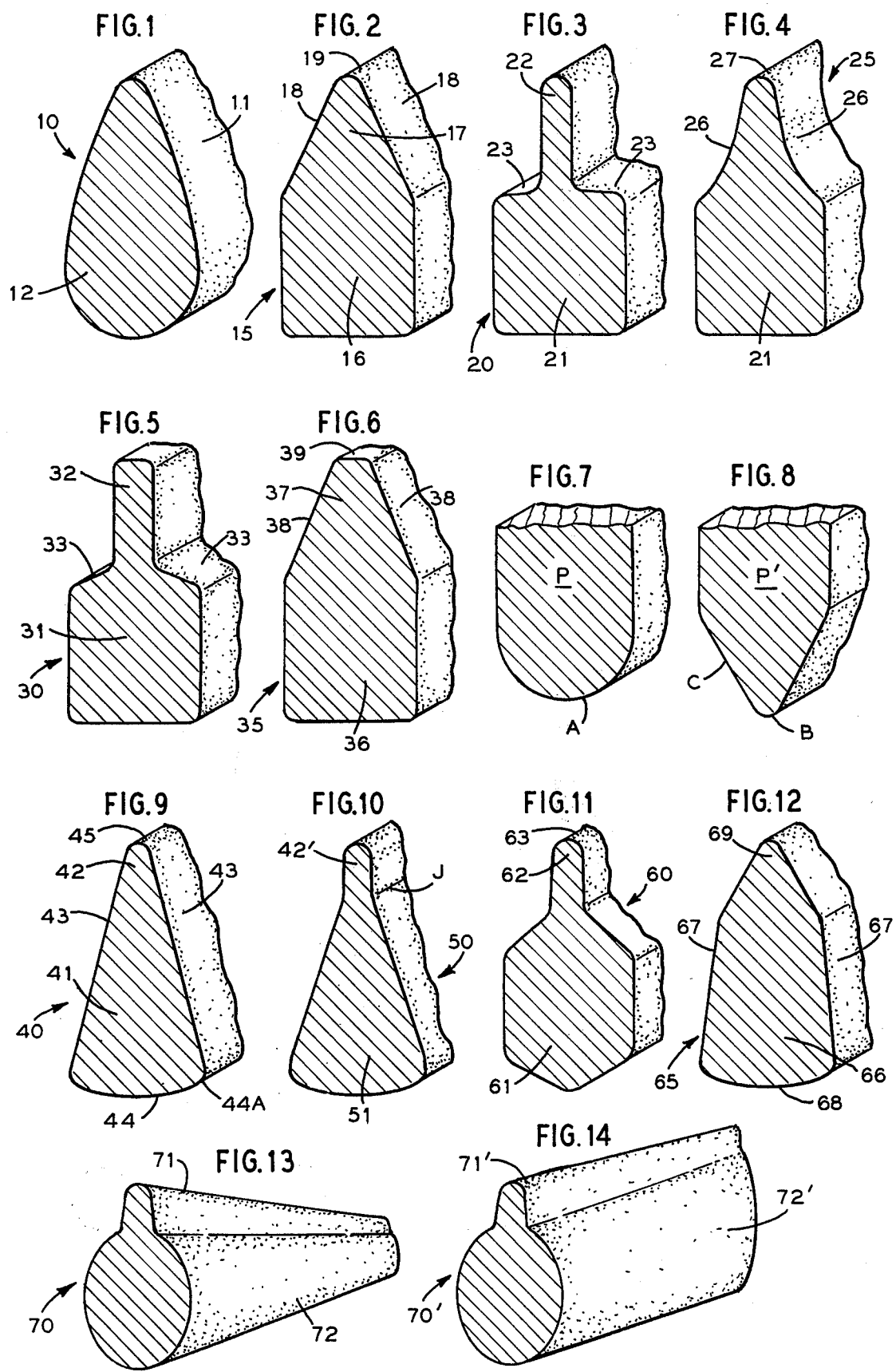

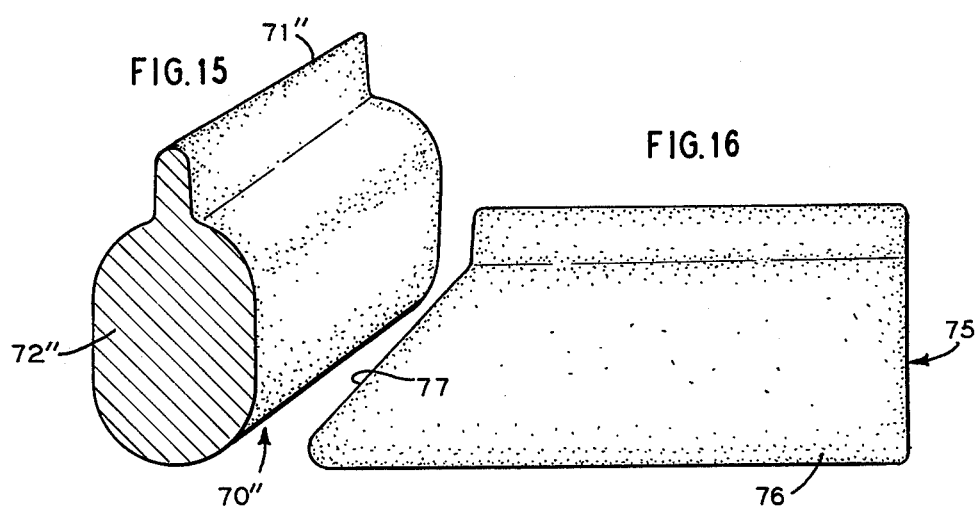
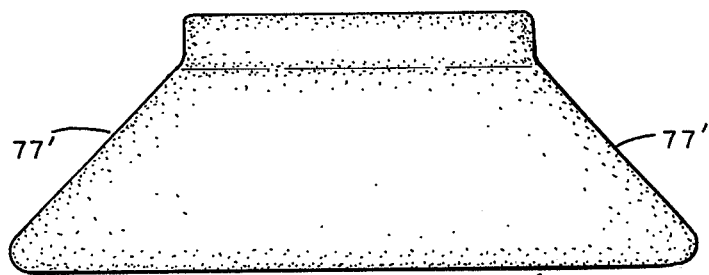
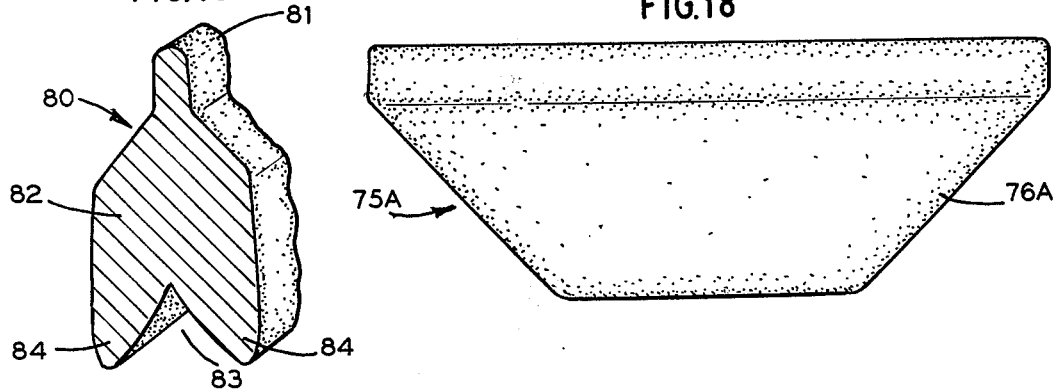
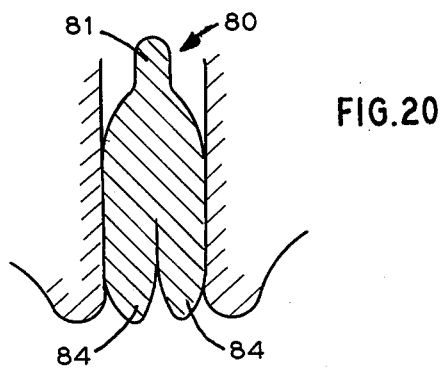

FEMININE HYGIENIC PAD

BACKGROUND OF THE INVENTION

It has been proposed to provide absorptive pads for use by females to absorb uncontrolled discharges such as urine, vaginal secretions, post-coital leakage, menstrual staining, or the like and is set forth in applicant's U.S. Pat. No. 3,726,277.

Such known absorptive pads are reasonably efficient in terms of ease of insertion, proper disposition in the interlabial space, and absorptive characteristics.

However, with widely varying conditions of uncontrolled discharge of various liquids, including urine, or the like; including total volume, rate of discharge, variations in anatomical dimensions in the interlabial space; known pads of given geometrical cross section and parameters may exhibit varying degrees of efficiency in actual use.

Accordingly, an object of this invention is to provide improved feminine hygienic pads for placement in the interlabial space to absorb uncontrolled discharges such as urine or the like; wherein the pads have selected geometrical cross sections which greatly facilitate the insertion of the pads into the interlabial space; are securely retained in the interlabial space; accomodate themselves to interlabial spaces of varying parameters; and maintain their retention in the interlabial space despite substantial increases in the weight of the pads due to absorption of the uncontrolled liquid discharge.

Another object of this invention is to provide an improved feminine hygienic pad having geometric cross sections distinguished by anterior leading edge portions of reduced transverse thickness and posterior portions of substantial transverse thickness; the anterior edge portions greatly facilitating the insertion of the pad into the interlabial space and the posterior portion having a high retention factor despite substantial amounts of liquid discharge absorbed by the posterior portion of the pad.

A further object of this invention is to provide an improved pad of the character described, wherein the juncture of the anterior and posterior portions thereof provide a substantially abrupt change in transverse dimensions, thereby forming a shoulderlike configuration at such juncture.

Yet another object of this invention is to provide an improved pad of the character described, wherein the anterior and posterior portions thereof may have planar surfaces.

Still another object of this invention is to provide pads of the character described, wherein the posterior portion thereof may be formed with a longitudinally extending groove such that upon insertion of the pad into the interlabial space, the posterior portions defining the groove therein, are pressed toward each other so as to resiliently provide a wedgelike retention characteristic with respect to the interlabial space.

Still a further object of this invention is to provide pads of the character described wherein the geometry of the cross section thereof is such that the axis of the combined anterior and posterior portions is relatively long whereas the transverse axis of the posterior portion is relatively short.

Still another object of this invention is to provide pads of the character described, wherein the cross section thereof may be of uniform dimensions along the length of the pad; or the cross section thereof may taper from one end to the other end of the pad. Further, one or both ends of the posterior portion of the pad may be sloped towards or away from the anterior portion.

Yet a further object of this invention is to provide pads of the character described, wherein the anterior portion of the pad is tapered along the length thereof, while the posterior portion remains of substantially uniform cross section along the length thereof.

Other objects of this invention will in part be obvious and in part hereinafter pointed out.

DESCRIPTION OF THE DRAWINGS

FIG. 1 is a cross sectional view of a feminine hygienic pad embodying the invention;

FIGS. 2–6 are cross sectional views of other alternative embodiments of the invention, in which the posterior portion of the pads is essentially of quadrilateral shape;

FIGS. 7 and 8 are cross sectional views of the posterior portions of pads embodying the invention wherein the bottom surfaces thereof may be arcuate or tapered;

FIGS. 9 and 10 are cross sectional views of other embodiments of the invention wherein the side surfaces of the posterior portions thereof slope toward the anterior portions thereof;

FIGS. 11–12 are cross sectional views showing still other embodiments of the invention wherein the posterior portions thereof have opposed flat surface portions;

FIGS. 13 to 15 are perspective views of pads embodying the invention, which include longitudinally tapering portions;

FIGS. 16–18 are side views of pads embodying the invention wherein the ends of the pads show sloping edges;

FIG. 19 is a perspective view of a pad embodying the invention wherein the posterior portion of the pad is formed with a longitudinal groove;

FIG. 20 is a cross sectional view showing the pad of FIG. 19 disposed in the interlabial space.

DESCRIPTION OF THE PREFERRED EMBODIMENTS

The hygienic pads of the instant invention comprise essentially soft absorptive bodies adapted to be inserted into the interlabial space for self retention therein, to absorb uncontrolled body discharges such as urine, vaginal exudates, menstrual staining, post-coital leakage, and the like.

It has been found that when such pads exhibit certain geometrical configurations; the pads are more readily inserted into the interlabial space by the user; are more securely retained in place despite substantial increases in weight due to absorption of the uncontrolled body discharges; and is more comfortable for the user thereof. Further the pads show an increased absorptive capacity, thereby decreasing the number of successive pad replacements.

The pads of the instant invention, hereinafter described in detail; are formed of soft absorptive material such as cellulose, cotton or other suitable natural or synthetic fibers or sheeting.

Thus, one embodiment of the invention is shown in FIG. 1, wherein an absorptive pad is indicated at 10. The pad 10 is of ovoid cross sectional shape and comprises a leading anterior edge portion 11 of limited transverse dimension and integral therewith a posterior portion 12 of relatively large transverse dimension.

The pad 10 may be of uniform cross section along the length thereof, or may be tapered from one end to the other end thereof. The user may readily and quickly insert the pad 10 into the interlabial space by way of the leading anterior portion 11. The pad is firmly self retained in the space and exhibits substantial absorptive capacity for liquid discharges and does not accidentally dislodge from the interlabial space.

Alternatively, the pads may have the posterior portions thereof of quadrilateral shape, such as rectangular or square. Thus, as shown in FIG. 2, pad 15 comprises the posterior portion 16 having flat bottom and side surfaces; and the anterior portion 17 having sloping surfaces 18 with a beveled edge 19.

Also, as shown in FIG. 3, the pad 20 comprises the posterior portion 21 of substantially square cross section; and a fingerlike anterior portion 22 of limited transverse dimension. The juncture 23 of portions 21, 22 is essentially flat. Pad 25, shown in FIG. 4 is similar to that of FIG. 3, except that the sides of anterior portion 26 diverge downwardly from top edge 27. The pad 30 shown in FIG. 5 has posterior portion 31 thereof and the anterior portion 32 thereof, quadrilateral in shape with a sloping flat shoulder 33 at the juncture of portions 31, 32. The pad 35 shown in FIG. 6, includes a posterior portion 36 of quadrilateral shape and an anterior portion 37 having upwardly converging side surfaces 38 and a flat leading edge 30.

While the pads shown in FIGS. 2–6 show their posterior portions with flat bottom surfaces; the bottom surfaces may have other configurations. Thus, as shown in FIG. 7, the posterior portion P has an arcuate bottom surface A, while in FIG. 8, the posterior portion P' has converging surfaces C and an arcuate bottom edge B.

Further, alternative embodiments are shown in FIGS. 9 and 10. Thus, in FIG. 9, the pad 40 is of generally triangular cross section, with a posterior portion 41 of large cross section and an anterior portion 42 of small cross section. The pad 40 shows flat, converging surfaces 43, a slightly curved bottom surface 44, rounded bottom edges 44A and a rounded leading edge 45. The pad 50, FIG. 10, is similar to pad 40, except that the anterior portion 42 is transversely constricted and provides a linear juncture J for posterior portion 51 and anterior portion 42'.

Pad 60, FIG. 11, comprises a posterior portion 61 of substantially hexagonal cross section and a transversely constricted anterior portion 62 with a rounded leading edge 63. The surfaces of posterior portion 61 are flat and edges thereof may be rounded.

Pad 65, FIG. 12 comprises a posterior portion 66 defined by opposed convergent flat surfaces 67 and a slightly rounded bottom surface 68; while anterior portion 69 is of a triangular cross section.

The pads may be suitably tapered. Thus, pad 70, FIG. 13 has its anterior portion 71 and posterior portion 72 tapered in respect of both the longitudinal and transverse axes thereof; whereas in pad 70', FIG. 14, anterior portion 71' and posterior portion 72' are tapered longitudinally only. Further, as shown in FIG. 15, pad 70'', the anterior portion 71'' and posterior portion 72'' are tapered with respect to their transverse axes only.

The pads may be further modified, as shown in FIGS. 16–18. Thus, as shown in FIG. 16, the pad 75 has its posterior portion 76 sloped at one end as at 77, to make the pad conform to the anatomy of the user; or as shown in FIG. 17, the pad 75' is sloped at opposite ends as at 77'. Alternatively, as shown in FIG. 18, pad 75A has its posterior portion 76A sloped at opposite ends in a convergent configuration. If desired, in the foregoing embodiments, the slope may also include the anterior portions of the pads.

The pads hereinbefore set forth, may be further modified as indicated in FIGS. 19, 20. Thus, as shown in FIG. 19, the pad 80 having anterior portion 81 and posterior portion 82; has the posterior portion 82 formed with a longitudinal groove 83 of normally triangular section, forming wings 84. When the pad 80 is inserted into the interlabial space, FIG. 20, the wings 84 are resiliently urged toward each other and bear against the walls of said interlabial space, thereby increasing the retention of the pad within the interlabial space. It is understood, that the various forms of pads set forth above, may also include the groove in the posterior portions thereof.

It will be understood, that the pads set forth above, having opposed flat surfaces, are particularly adapted to conform to the walls defining the interlabial space; thereby optimizing the retention and absorption factors of the pads.

The tapered pads hereinabove set forth, which taper from one end to the other end thereof; may also taper from a central portion to the opposite ends thereof.

I claim:

1. A unitary elongated absorbent pad insertable in its entirety into the interlabial space to receive uncontrolled discharges, said pad comprising a means to be snuggly received in and block the interlabial space including a longitudinally extending posterior portion and a longitudinally extending anterior portion integrated with said posterior portion, said anterior portion having a limited transverse sectional dimension relative to a larger transverse sectional dimension of said posterior portion and, upon insertion facing the vestibule, facilitating insertion of the entire pad into the interlabial space with the transversely larger posterior portion being led therein by the anterior portion, the inserted posterior portion facing outward toward the opening of the interlabial space, and wherein the geometry of the cross section of said pad is such that the axis of the combined anterior and posterior portions is relatively long whereas the transverse axis of the posterior portion is relatively short, providing a shape substantially contiguous with the walls of said interlabial space to substantially fill said space.

2. A pad as in claim 1 wherein said posterior portion has longitudinally extending, opposed substantially parallel face portions.

3. A pad as in claim 1 wherein said posterior portion has longitudinally extending, face portions converging toward said anterior portion.

4. A pad as in claim 1 wherein said posterior portion has opposed flat surface portions.

5. A pad as in claim 1 wherein said anterior portion has opposed flat surface portions.

6. A pad as in claim 5 wherein said opposed flat surface portions are substantially parallel.

7. A pad as in claim 5 wherein said opposed flat surface portions are substantially convergent.

8. A pad as in claim 1 wherein the juncture of said anterior and posterior portions is in shoulder form.

9. A pad as in claim 8 wherein the juncture of the anterior and posterior portions is defined by flat surface portions extending at an angle to each other.

10. A pad as in claim 1 wherein said posterior portion comprises a series of flat surface portions angularly related to each other.

11. A pad as in claim 1 wherein said posterior portion comprises a flat bottom face.

12. A pad as in claim 1 wherein said anterior portion comprises opposed flat surface portions in convergent relation to each other.

13. A pad as in claim 12 wherein the longitudinally extending top edge of said anterior portion is of arcuate cross section.

14. A pad as in claim 1 wherein the bottom face of said posterior portion is of arcuate cross section.

15. A pad as in claim 1 wherein said posterior portion is of arcuate cross section.

16. A pad as in claim 1 wherein said posterior portion is formed with a longitudinally extending groove, said groove extending inwardly from the bottom surface of said posterior portion.

17. A pad as in claim 1 wherein the transverse cross section tapers from one end of said pad to the other end thereof.

18. A pad as in claim 17 wherein the cross section of the anterior portion tapers vertically along the longitudinal extent thereof.

19. A pad as in claim 17 wherein the cross section of the anterior portion tapers transversely along the longitudinal extent thereof.

20. A pad as in claim 1 wherein at least one end thereof comprises convergent face portions.

21. A pad as in claim 1 wherein at least one end of said posterior portion includes an edge portion sloping toward said anterior portion.

22. A pad as in claim 1 wherein the cross section thereof is of ovoid shape, the anterior portion being of minimal dimensions and the posterior portion being of maximum dimensions.

23. A pad as in claim 1 wherein the posterior portion, in cross-section, tapers toward the outward bottom face thereof to allow a drawing together of the labia over the inserted pad to facilitate retention thereof.

* * * * *